United States Patent
Kurokawa et al.

[11] Patent Number: 5,527,927
[45] Date of Patent: Jun. 18, 1996

[54] PROCESS FOR PRODUCING GLYCIDYL ACRYLATE OR GLYCIDYL METHACRYLATE

[75] Inventors: Masahiro Kurokawa; Akihiro Honma; Tsuyoshi Isozaki, all of Hiratsuka, Japan

[73] Assignee: Mitsubishi Gas Chemical Company, Inc., Tokyo, Japan

[21] Appl. No.: 438,345

[22] Filed: May 10, 1995

[30] Foreign Application Priority Data

May 20, 1994 [JP] Japan ................... 6-106619

[51] Int. Cl.$^6$ .............. C07D 301/00; C07D 301/36; C07D 303/16
[52] U.S. Cl. .............................. 549/539; 549/541
[58] Field of Search ............................... 549/539

[56] References Cited

U.S. PATENT DOCUMENTS

| | | | |
|---|---|---|---|
| 3,255,162 | 6/1966 | Beavers et al. | 549/539 |
| 4,228,084 | 10/1980 | Ackermann et al. | 549/539 |
| 4,285,872 | 8/1981 | Tanabe et al. | 549/539 |
| 4,418,204 | 11/1983 | Arndt et al. | 549/539 |
| 4,667,044 | 5/1987 | Nees et al. | 549/539 |
| 4,755,262 | 7/1988 | Matsunaga et al. | |

FOREIGN PATENT DOCUMENTS

| | | | |
|---|---|---|---|
| 3120263 | 5/1991 | Japan | 549/539 |
| 6001780 | 1/1994 | Japan | 549/539 |

OTHER PUBLICATIONS

DATABASE WPI, Derwent Publications Ltd., London, GB; AN 92–255691 of JP-A-4 173 783 (DAICEL CHEM IND LTD) (1992).

DATABASE WPI, Derwent Publications Ltd., London, GB; AN 94–086021 of JP-A-6 001 780 (DAICEL CHEM IND LTD) (1994).

DATABASE WPI, Derwent Publications Ltd., London, GB; AN 77–09999Y of JP-A∝51 148 792 (Toray Inds KK) (1996).

DATABASE WPI, Derwent Publications Ltd., London, GB; AN 80–61353C of JP-A-55 094 379 (DAICEL KK) (1980).

J. I. Luengo et al., "Effcient removal of pipecolinate from rapamycin and FK506 by reaction with n–Bu4N+ CN–", TETRAHEDRON LETTERS, vol. 34, No. 29, 16 Jul. 1993, OXFORD GB pp. 4599–4602.

Primary Examiner—Joseph E. Evans
Attorney, Agent, or Firm—Frishauf, Holtz, Goodman, Langer & Chick

[57] ABSTRACT

There are disclosed a process for producing glycidyl acrylate or glycidyl methacrylate by the transesterification of glycidol and methyl methacrylate, etc. which process comprises carrying out the transesterification in the presence of a polymerization inhibitor by using, as a catalyst, a quaternary ammonium salt represented by the general formula (I) or a quaternary phosphonium salt represented by the general formula (II)

$$(R^1R^2R^3R^4)NX \quad (I)$$

$$(R^1R^2R^3R^4)PX \quad (II)$$

wherein $R^1$, $R^2$, $R^3$ and $R^4$ are each an alkyl group having 1 to 20 carbon atoms, or the like, and X is a cyanide ion, cyanate ion or the like to complete the reaction; thereafter arresting the reaction by adding a catalyst deactivator represented by the general formula (III)

$$SB \quad (iii)$$

wherein S is a sulfonic acid or a heteropolyacid and B is an alkali metal excluding potassium or an alkaline earth metal; and distilling away unreacted methyl methacrylate, etc. under reduced pressure and two similar modified processes. The processes can produce highly pure glycidyl methacrylate, etc. substantially free from a chlorine component and the processes can enhance the conversion of glycidol without lowering the purity and yield of the objective product.

16 Claims, No Drawings

PROCESS FOR PRODUCING GLYCIDYL ACRYLATE OR GLYCIDYL METHACRYLATE

BACKGROUND OF THE INVENTION

1. Field of the Invention

The present invention relates to a process for producing glycidyl acrylate or glycidyl methacrylate (hereinafter sometimes collectively referred to as "glycidyl methacrylate, etc.") by reacting glycidol with methyl acrylate or methyl methacrylate (hereinafter sometimes collectively referred to as "methyl methacrylate, etc.") in the presence of a transesterification catalyst. Glycidyl methacrylate, etc. are widely used as starting raw materials for industrial use for resin modifieres, thermosetting coating materials, adhesives, textile treating agents, antistatic agents, ion exchange resins and the like.

In particular, glycidyl methacrylate, etc. with a minimized content of chlorine have recently been required in the fields of coating materials (especially powdery coating materials), electronic materials, textile materials and the like.

2. Description of the Related Arts

Glycidyl methacrylate, etc. are generally produced by a process in which acrylic acid or methacrylic acid is reacted with an alkali to form an alkali salt of acrylic acid or methacrylic acid, which is then reacted with epichlorohydrin in the presence of a quaternary ammonium salt, followed by dehydrochlorination.

The glycidyl methacrylate, etc. that are produced by the above-mentioned process usually contain residual chlorine compounds in an amount of about 1,000 to 10,000 ppm expressed in terms chlorine concentration. The aforesaid residual chlorine components not only bring about the deterioration of coating material properties, electrical properties and the problem of eruption on the skin in the fields of coating materials (for example, powdery coating materials), electronic materials, textile materials and the like but also involve a fear of carcinogenicity in recent years. Under such circumstances, it is required to improve the working environment where any of the above-mentioned materials is dealt with.

That is to say, the aforestated chlorine compounds contained as impurities are responsible for the deterioration of the performance of the resins themselves containing the glycidyl methacrylate, etc. and also the coating materials etc. as the purpose of use of the resins.

It is preferable therefore, that the chlorine compounds as impurities be removed as much as possible from the glycidyl methacrylate, etc. thus produced. However, the glycidyl methacrylate, etc. that are produced by the foregoing process usually contain residual chlorine components in an amount of several thousands ppm as chlorine, against which any effective method for removal is not proposed at all.

As a process for producing the glycidyl methacrylate, etc. free from a chlorine compound which process is different from the aforesaid process, there is available a process for producing the same by the transesterification of glycidol and methyl methacrylate, etc. It is thought that the glycidyl methacrylate, etc. produced by the transesterification is substantially free from a chlorine component, and is capable of greatly improving the deterioratin of amount of the of the resin modified therewith, toxicity thereof and environmental problems.

As a process for producing glycidyl methacrylate, etc. by the above-mentioned transesterification, there is disclosed, in Japanese Patent Publication No.38421/1972, a process in which the reaction is carried out in the presence of a phosphine as a catalyst. However, the amount of the production of glycidyl methacrylate as described therein is such that it was observed on the gas chromatograph, thereby making the process insignificant from the viewpoint of industrial production in general.

Japanese Patent Publication No.6133/1978 describes that the use of potassium cyanide as a catalyst enables the transesterification to proceed in a conversion of glycidol of 98%. Nevertheless, there are formed during the reaction, a Michael adduct of glycidol or methanol with methyl methacrylate or glycidyl methacrylate and an addition reaction product of a compound having an epoxy group such as glycidol and glycidyl methacrylate, and after the completion of the reaction, there is formed black to blackish brown precipitates in the form of solid or oil, which must be removed from the reaction system prior to the distillating purification of the glycidyl methacrylate, etc. The procedure not only complicates the production process but also lowers the purity of the objective product to be obtained by the regeneration of glycidol at the time of distillating glycidyl methacrylate, etc.

In addition, Japanese Patent Publication No.37268/1986 describes that glycidyl methacrylate is produced in a yield of 95% by synthesizing the same by the use of a strong alkali catalyst such as sodium methylate and immediately thereafter, removing the formed methanol under reduced pressure. However, the industrial use of such a catalyst is accompanied by considerable danger, since the catalyst must be filtered prior to the distillating purification of glycidyl methacrylate and in addition, a sodium alcoholate is generally an anion polymerization initiator for methacrylic acid esters.

On the other hand, Japanese Patent Application Laid-Open No.173783/1992 discloses in Comparative Example 3 of the specification, that glycidyl methacrylate is produced by dissolving potassium acetate as a catalyst in glycidol and adding the resultant solution dropwise in methyl methacrylate to cause the reaction. In the aforestated process, however, potassium acetate as a catalyst must be filtered after the completion of the reaction, and even if it is filtered, a slight amount of the catalyst thus dissolved causes the by-production of glycidol in the latter period of distillation for recovering glycidyl methacrylate, thereby markedly lowering the purity of the objective glycidlyl methacrylate.

Moreover, the use of patassium acetate as a catalyst suffers the disadvantage that it is necessary to provide a dissolving tank for dissolving potassium acetate in glycidol, while glycidol should be preserved at a low temperature, since it is made instable in the presence of potassium acetate.

Japanese Patent Application Laid-Open No.1780/1994 discloses in Example 1 of the specification, that glycidyl methacrylate is produced in high purity (98.9%) by a process in which triethylamine is employed as a catalyst, methanol which is formed by the reaction of glycidol and methyl methacrylate is rapidly distilled away by means of hexane, the conversion of glycidol is enhanced by the distillation wi...e suppressing the formation of the adduct of methanol to methyl methacrylate and further suppressing the formation of glycidol in the latter period of the distillation.

Nevertheless, the above-disclosed process is disadvantageous in that it necessitates, in addition to glycidol and methyl methacrylate as principal staring raw material, hexane for removing methanol, thereby deteriorating the yield in a kettle; that it is required to carry out the purity regulation of methyl methacrylate to be recovered and reused, at every time of recovery because of hexane contained therein, thus complicating the procedure; that the amount of triethylamine contained in methyl methacrylate to be recovered and reused must be always checked, though it is explained that the triethylamine as a catalyst is removed at the time of recovering methyl methacrylate; and that a slight amount of amine is thought to be mixed in the objective glycidyl methacrylate, thereby decisively deteriorating the quality of the glycidyl methacrylate.

Although being independent of the transesterification catalyst according to the present, there are introduced quaternary ammonium salts and quaternary phosphonium salts as phase-transfer catalysts for the purpose of producing an alkyl cyanide by reacting sodium cyanide in a water layer with an alkyl halide in an oil layer. (Refer to Journal of the American Chemical Society, vol. 93, p. 195, Jan. 13, 1971.)

SUMMARY OF THE INVENTION

It is a general object of the present invention to provide a process for producing glycidyl methacrylate, etc. by solving the problems associated with the prior arts and enhancing the reactional efficiency of glycidol without deteriorating the purity of the objective product in the course of purification.

As a result of intensive research and investigation made by the present inventors, it has been found that glycidyl acrylate or glycidyl methacrylate is produced with high purity by carrying out the transesterification in the presence of a polymerization inhibitor and a specific quaternary ammonium salt or a specific quaternary phosphonium salt as a catalyst to complete the reaction and thereafter arresting the reaction through the addition of a catalyst deactivator. The present invention has been accomplished on the basis of such finding.

Specifically, the present invention provides a process for producing glycidyl acrylate or glycidyl methacrylate by the transesterification of glycidol and methyl acrylate or methyl methacrylate which process comprises carrying out the transesterification to complete the reaction in the presence of a polymerization inhibitor by the use of a catalyst selected from the group consisting of a quaternary ammonium salt represented by the general formula (I) and a quaternary phosphonium salt represented by the general formula (II)

$(R^1R^2R^3R^4)NX$  (I)

$(R^1R^2R^3R^4)PX$  (II)

wherein $R^1$, $R^2$, $R^3$ and $R^4$ are each an alkyl group having 1 to 20 carbon atoms, an alkenyl group or a phenyl group and X is a cyanide ion, cyanate ion, an organocarboxylate ion or a thiocyanate ion; thereafter arresting the reaction by adding to the reaction system a catalyst deactivator represented by the general formula (III)

SB  (III)

wherein S is a sulfonic acid or a heteropolyacid and B is an alkali metal with the proviso that potassium is excluded therefrom or an alkaline earth metal; and distilling away unreacted methyl acrylate or methyl methacrylate under reduced pressure to separate glycidyl acrylate or glycidyl methacrylate.

The catalyst represented by the general formula (I) or (II) is added to the reaction system composed of glycidol and methyl methacrylate, etc. and acts as a transesterification catalyst.

On the other hand, the catalyst deactivator represented by the general formula (III) is added to the reaction system after the completion of the reaction for the purpose of deactivating the catalyst, and subjecting the catalyst to double decomposition as indicated by the reactional formula. The double decomposition products do not exhibit at all an activity as a transesterification catalyst.

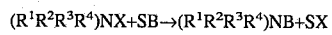

$(R^1R^2R^3R^4)NX+SB \rightarrow (R^1R^2R^3R^4)NB+SX$

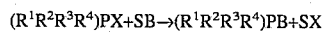

$(R^1R^2R^3R^4)PX+SB \rightarrow (R^1R^2R^3R^4)PB+SX$

That is to say, one of the features of the present invention resides in that the catalyst to be used exhibits an activity as a transesterification catalyst in the synthesis step, whereas immediately after the completion of the reaction it is completely deactivated, thus making it possible to produce highly pure glycidyl methacrylate, etc.

In the quaternary ammonium salt represented by the general formula (I) and the quaternary phosphonium salt represented by the general formula (II) that are used in the present invention, $R^1$, $R^2$, $R^3$ and $R^4$ are each an alkyl group having 1 to 20 carbon atoms, an alkenyl group or a phenyl group and specifically exemplified by methyl group, ethyl group, propyl group, butyl group, allyl group, phenyl group and alkyl-substituted phenyl group, X is a cyanide ion, cyanate ion, an organocarboxylate ion or thiocyanate ion. The organocarboxylate ion is exemplified by formate ion, acetate ion, propionate ion, methacrylate ion and benzoate ion.

Specific examples of the quaternary ammonium salts represented by the general formula (I) include tetramethylammonium acetate, tetraethylammonium acetate, tetramethylammonium cyanide, tetraethylammonium cyanide, tetrabutylammonium acetate, tetrabutylammonium cyanide, tetrabutylammonium thiocyanate, trimethylethylammonium cyanide, dimethyldiethylammonium acetate, methyltriethylammonium thiocyanate, trimethylbenzylammonium acetate, triethylbenzylammonium cyanide and tetramethylammonium methacrylate. Specific examples of the quaternary phosphonium salt represented by the general formula (II) include tetramethylphosphonium methacrylate and tetraphenylphosphonium cyanide. The present invention, however, is not restricted to the above-exemplified species.

Any of the quaternary ammonium salt represented by the general formula (I) and the quaternary phosphonium salt represented by the general formula (II) as catalysts may be used alone or in combination with at least one other one. The catalyst may be used in the form of solid or aqueous solution.

Examples of the catalyst deactivator represented by the general formula (III) to be employed in the present invention include a sodium salt of any of methanesulfonic acid, methallylsulfonic acid, octylsulfonic acid and laurylsulfonic acid, an alkali metal salt excluding potassium salt of any of p-toluenesulfonic acid, dodecylbenzenesulfonic acid, xylenesulfonic acid, naphthalenesulfonic acid, phosphotungstic acid and phosphomolybdic acid and alkaline earth metal salt of any of the above-mentioned acids.

The above-exemplified catalyst deactivator may be used alone or in combination with at least one other one.

As mentioned hereinbefore, the present invention is characterized in that the transesterification of glycidol with methyl methacrylate, etc. is completed within a short time with minimized formation of impurities in the presence of a polymerization inhibitor by the use of a quaternary ammonium salt (for example, tetraethylammonium cyanide) as a catalyst and immediately thereafter the catalyst is deactivated by adding a catalyst deactivator (for example, sodium p-toluenesulfonate and sodium phosphotungstinate), while completely suppressing the formation of glycidol during the distillation of glycidyl methacrylate, etc.

The adoption of the production process according to the present invention has made it possible to easily produce glycidyl methacrylate, etc. with high purity of substantially at least 98.0% or 98.5% and at the same time to produce glycidyl acrylate or glycidyl methacrylate completely free from a chlorine compound which has heretofore been regarded as an impurity inherent to an epoxy compound to be used in the reaction. In addition, the process according to the present invention has solved the problems with the conventional process of producing glycidyl methacrylate, etc. using glycidol such as low reaction efficiency or conversion; the formation of impurities derived from the catalyst; the deterioration of the yield and purity of the objective glycidyl methacrylate, etc. owing to the formation of a Michael adduct of methanol formed by the transesterification, methyl methacrylate, etc. and glycidyl methacrylate, etc.; and the trouble of regenerating glycidol and decrease in the purity and yield of glycidyl methacrylate, etc. in the case where a solid catalyst frequently used in the conventional process is present at the time of distilling glycidyl methacrylate, etc.

On the other hand, the use of publicly known potassium cyanide as a catalyst for the transesterification results in failure to exert the working effect of the present invention.

As the other process (the second process) of the present invention, a specific aqueous solution may be used in place of the above-mentioned process (the first process) of the present invention.

The second process according to the present invention relates to a process for producing glycidly methacrylate, etc. by the transesterification of glycidol and methyl methacrylate, etc. which process comprises carrying out the transesterification in the presence of a polymerization inhibitor by the use of, as a catalyst, an aqueous solution containing KX represented by the General formula (IV)

KX　　　　　　　　　　　　　　　　　　(IV)

wherein K is potassium and X is a cyanide ion, cyanate ion, an organocarboxylate ion or a thiocyanate ion, and a salt selected from the Group consisting of a quaternary ammonium salt represented by the General formula (V) and a quaternary phosphonium salt represented by the General formula (VI)

$(R^1R^2R^3R^4)NY$　　　　　　　　　　(V)

$(R^1R^2R^3R^4)PY$　　　　　　　　　　(VI)

wherein $R^1$, $R^2$, $R^3$ and $R^4$ are each an alkyl group having 1 to 20 carbon atoms, an alkyenyl group or a phenyl group and Y is iodine, bromine or chlorine, to complete the reaction; thereafter arresting the reaction by adding to the reaction system, a catalyst deactivator represented by the general formula (III)

SB　　　　　　　　　　　　　　　　　　(III)

wherein S is a sulfonic acid or a heteropolyacid and B is an alkali metal with the proviso that potassium is excluded therefrom or an alkaline earth metal; and distilling away unreacted methyl acrylate or methyl methacrylate under reduced pressure to separate glycidyl acrylate or glycidyl methacrylate.

Examples of the KX represented by the general formula (IV) to be used in the second process of the present invention include potassium cyanide, potassium cyanate, potassium thiocyanate, potassium methacrylate, potassium acetate, potassium formate, potassium propionate and potassium benzoate. The KX may be used alone or in combination with at least one other arbitrary KX.

The quaternary ammonium salt represented by the general formula (V) is exemplified by tetramethylammonium chloride, trimethylethylammonium chloride, dimethyldiethylammonium chloride, methyltriethylammonium chloride, tetraethylammonium chloride, trimethylbenzylammonium chloride and triethylbenzylammonium chloride. The quaternary phosphonium salt represented by the general formula (VI) is exemplified by but not limited to tetramethylphosphonium iodide and tetraphenylphosphonium chloride.

Any of the quaternary ammonium salt and the quaternary phosphonium salt may be used alone or in combination with at least one other one.

The suitable examples of the catalyst deactivator represented by the general formula (III) to be employed in the second process of the present invention include the SB to be used in the above-mentioned first process, that is, a sodium salt of any of methanesulfonic acid, methallylsulfonic acid, octylsulfonic acid, laurylsulfonic acid, p-toluenesulfonic acid, dodecylbenzenesulfonic acid, xylenesulfonic acid and naphthalenesulfonic acid, an alkali metal salt (excluding potassium salts) of any of phosphotungstic acid and phosphomolybdic acid and an alkaline earth metal salt of any of the above-exemplified acid. The catalyst deactivator as exemplified above may be used alone or in combination with at least one other one.

The second process of the present invention is characterized in that the transesterification of glycidol with methyl methacrylate, etc. is completed within a short time with minimized formation of impurities in the presence of a polymerization inhibitor by the use of a catalyst comprising, for example, a mixed aqueous solution of potassium cyanide and tetramethylammonium chloride and thereafter the catalyst is deactivated by adding a catalyst deactivator, for example, sodium p-toluenesulfonate, while completely suppressing the formation of glycidol during the distillation of glycidol methacrylate, etc. In more detail of the process, the potassium cyanide in the aqueous solution of itself with tetramethylammonium chloride is subjected to double decomposition to form tetramethylammonium cyanide and potassium chloride and the resultant tetramethylammonium cyanide acts as a transesterification catalyst. By adding sodium p-toluenesulfonate after the completion of the transesterification, the tetramethylammonium cyanide as a catalyst is subject to double decomposition into sodium cyanide and p-toluenesulfonic acid salt of tetramethylammonium, whereby the catalyst is completely deactivated.

By the deactivation, the by-production of glycidol is completely prevented at the time of distillation, especially the latter period of distillation of glycidyl methacrylate, etc., thus enabling as a result, to produce glycidyl methacrylate, etc. with high purity of at least 98% or 98.5%.

As is the case with the first process of the present invention, the second process thereof has also solved the problems with the conventional process of producing glycidyl methacrylate, etc. such as low reaction efficiency or conversion; the formation of impurities derived from the catalyst; the deterioration of the yield and purity of the objective glycidyl methacrylate, etc. owing to the formation of a Michael adduct of methanol formed by the transesterification and methyl methacrylate, etc. or glycidyl methacrylate, etc.; and decrease in the purity and yield of glycidyl methacrylate, etc. due to the regeneration of glycidol in the case where glycidyl methacrylate, etc. is distilled in the presence of a solid catalyst which has frequently been used in the conventional process.

In the second process, the use of potassium cyanide (KCN) corresponding to KX of the general formula (IV) alone as a catalyst results in failure to exert the working effect of the present invention.

As the another process (the third process) of the present invention, specific reactants may be used in place of the catalyst of the first process. The third process according to the present invention relates to a process for producing glycidyl methacrylate, etc. by the transesterification of glycidol and methyl methacrylate, etc. which process comprises carrying out the transesterification in the presence of a polymerization inhibitor by the use of a catalyst comprising KX represented by the general formula (IV)

$$KX \quad\quad\quad\quad (IV)$$

wherein K is potassium and X is a cyanide ion, cyanate ion, an organocarboxylate ion or a thiocyanate ion, and a salt selected from the group consisting of a quaternary ammonium salt represented by the general formula (V) and a quaternary phosphonium salt represented by the general formula (VI)

$$(R^1R^2R^3R^4)NY \quad\quad (V)$$

$$(R^1R^2R^3R^4)PY \quad\quad (VI)$$

wherein $R^1$, $R^2$, $R^3$ and $R^4$ are each an alkyl group having 1 to 20 carbon atoms, an alkenyl group or a phenyl group and Y is iodine, bromine or chlorine, to complete the reaction; thereafter arresting the reaction by adding to the reaction system, a catalyst deactivator represented by the general formula (III)

$$SB \quad\quad\quad\quad (III)$$

wherein S is a sulfonic acid or a heteropolyacid and B is an alkali metal with the proviso that potassium is excluded therefrom or an alkaline earth metal; and distilling away unreacted methyl methacrylate, etc. under reduced pressure to separate from the glycidyl methacrylate, etc.

The third process will be explained in the following through reaction formulae.

The KX represented by the general formula (IV) and $(R^1R^2R^3R^4)NY$ represented by the general formula (V) or $(R^1R^2R^3R^4)PY$ represented by the general formula (VI) are subjected to double decomposition according to the following reaction formulae to form $(R^1R^2R^3R^4)NX$ or $(R^1R^2R^3R^4)PX$, which exhibits an activity as a new catalyst.

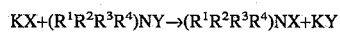

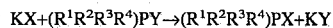

In order to deactivate the aforesaid catalyst comprising $(R^1R^2R^3R^4)NX$ or $(R^1R^2R^3R^4)PX$ upon the completion of the reaction, the catalyst deactivator represented by the general formula (III) is added to the reaction system to proceed with double decomposition according to the following reaction formulae. The double decomposition products thus formed do not exhibit a activity at all as a transesterification catalyst.

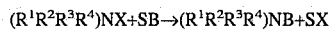

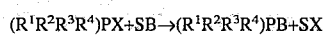

That is to say, glycidyl methacrylate, etc. with high purity of substantially at least 98.0% or 98.5% by weight is easily obtained by adopting the third process of the present invention, specifically by completely deactivating through double decomposition, upon the completion of the reaction, the catalyst which exhibited sufficient activity for transesterification in the synthesis step. In addition, the third process has made it possible to produce glycidyl acrylate or glycidyl methacrylate completely free from a chlorine compound which has heretofore been regarded as impurity inherent to an epoxy compound to be used in the reaction.

The KX to be used is exemplified by potassium cyanide, potassium cyanate, potassium acetate, potassium methacrylate, potassium formate, potassium propionate, potassium benzoate and potassium thiocyanate, any of which may be used alone or in combination with at least one other orditrary KX.

The quaternary ammonium salt to be used in the third process is exemplified by tetramethylammonium chloride, trimethylethylammonium chloride, dimethyldiethylammonium chloride, methyltriethylammonium chloride, tetraethylammonium chloride, trimethylbenzylammonium chloride and triethylbenzylammonium chloride. The quaternary phosphonium salt to be used in the third process is exemplified by tetramethylphosphonium iodide and tetraphenylphosphonium chloride.

Any of the quaternary ammonium salt and the quaternary phosphonium salt may be used alone or in combination with at least one other one.

The suitable examples of the catalyst deactivator represented by the general formula (III) to be employed in the third process of the present invention include the SB to be used in the above-mentioned first or second process, that is, a sodium salt of any of methanesulfonic acid, methallylsulfonic acid, octylsulfonic acid, laurylsulfonic acid, p-toluenesulfonic acid, dodecylbenzenesulfonic acid, xylenesulfonic acid, naphthalenesulfonic acid, phosphotungstic acid and phosphomolybdic acid. The catalyst deactivator as exemplified above may be used alone or in combination with at least one other one.

The third process of the present invention is characterized in that the transesterification of glycidol with methyl methacrylate, etc. is completed within a short time with minimized formation of impurities in the presence of a polymerization inhibitor by the use of a highly active catalyst, for example, potassium cyanide and tetramethylammonium chloride and thereafter the catalyst is deactivated by adding a catalyst deactivator, for example, sodium p-toluenesulfonate and sodium phosphotungstate, while completely suppressing the formation of glycidol during the distillation of glycidol methacrylate, etc. In more detail of the activation and deactivation process, the potassium cyanide and a tetraalkylammonium chloride are subjected to double decomposition to form tetraalkylammonium cyanide and potassium chloride and the resultant tetraalkylammonium cyanide acts as a transesterification catalyst. By adding sodium p-toluenesulfonate immediately after the completion of the transesterification, the tetraalkylammonium cyanide as a catalyst is subject to double composition into sodium cyanide and p-toluensulfonic acid salt of tetraalkylammonium, whereby the catalyst is completely deactivated.

It is completely ineffective in the transesterification to use potassium cyanide alone and add the catalyst deactivator upon the completion of the reaction.

By adopting this deactivation step, the by-production of glycidol is completely prevented at the time of distillation, especially the latter period of distillation of glycidyl methacrylate, etc., thus enabling as a result, to produce glycidyl methacrylate, etc. with high purity of at least 98% or 98.5%.

As is the case with the first or second process of the present invention, the third process thereof has also solved the problems with the conventional process of producing glycidyl methacrylate, etc. such as low reation efficiency or conversion; the formation of impurities derived from the catalyst; the deterioration of the yield and purity of the objective glycidyl methacrylate, etc. owing to the formation of a Michael adduct of methanol formed by the transesterification and methyl methacrylate, etc. and glycidyl methacrylate; and decrease in the purity and yield of glycidyl methacrylate, etc. due to the regeneration of glycidol in the case where glycidyl methacrylate, etc. is distilled in the presence of a solid catalyst which has frequently been used in the conventional process.

DESCRIPTION OF PREFERRED EMBODIMENT

In the first process of the present invention, the quaternary ammonium salt represented by the general formula (I) or the quaternary phosphonium salt represnted by the general formula (II) is added to the reaction system containing glycidol and methyl methacrylate, etc. and acts as a transesterification catalyst. Moreover, the catalyst deactivator represented by the general formula (III) acts so as to deactivate the transesterification catalyst after the completion of the transesterification.

Of the above-exemplified quaternary ammonium salts represented by the general formula (I), examples of the. preferably usable one include at least one member selected from the group consisting of tetramethylammonium acetate, tetramethylammonium cyanide, tetramethylammonium methacrylate and tetrabutylammonium cyanide. Examples of the preferably usable quaternary phosphonium salts include at least one member selected from the group consisting of those as exemplified hereinbefore.

The blending proportion of the quaternary ammonium salt represented by the general formula (I) or the quaternary phosphonium salt represented by the general formula (II) is preferably 1 to 500 mmol, more preferably 3 to 100 mmol, particularly preferably 5 to 50 mmol per 1 mol of glycidol as a staring reactional material. In the case where the catalyst is employed in the form of aqueous solution, the concentration of the solution is preferably 30 to 80% by weight from the practical point of view.

The catalyst deactivator is preferably at least one member selected from the group consisting of an alkali metal salt (excluding potassium salt) and an alkaline earth metal salt of any of an alkylsulfonic acid, alkylbenzenesulfonic acid, a phosphotungstic acid and phosphomolybdic acid and is specifically exemplified by, as a preferably usable one, at least one member selected from the group consisting of sodium p-toluenesulfonate, sodium phosphotungstate and sodium phosphomolybdate. The amount of the catalyst deactivator to be used is preferably 1 to 1000 mmol, more preferably 3 to 200 mmol, particularly preferably 5 to 100 mmol per 1 mol of glycidol.

In the second process of the present invention, an aqueous solution containing the compound represented by the general formula (IV) and the quaternary ammonium salt represented by the general formula (V) or the quaternary phosphonium salt represented by the general formula (VI) is added to the reaction system containing glycidol and methyl methacrylate, etc. to cause the transesterification. The catalyst deactivator represented by the general formula (III) to be added to the reaction system upon the completion of the reaction functions so as to deactivate the above-mentioned transesterification catalyst.

In the second process, the KX represented by the general formula (IV) is selected from the group consisting of potassium cyanide, potassium cyanate, potassium organocarboxylate and potassium thiocyanate. Preferable potassium organocarboxylates are potassium methacrylate, potassium acetate, potassium formate and potassium benzoate.

The blending proportion of the KX to be used is preferably 1 to 500 mmol, more preferably 3 to 100 mmol, particularly preferably 5 to 50 mmol per 1 mol of glycidol.

Of the above-exemplified preferable quaternary ammonium salts represented by the general formula (V) including tetramethylammonium chloride, trimethylethylammonium chloride, dimethyldiethylammonium chloride, methyltriethylammonium chloride, tetraethylammonium chloride, trimethylbenzylammonium chloride and triethylbenzylammonium chloride, there are particularly preferably usable tetramethylammonium chloride, methyltriethylammonium chloride, tetraethylammonium chloride and triethylbenzylammonium chloride. Of the above-exemplified preferable quaternary phosphonium salt represented by the general formula (VI) including tetramethylphosphonium iodide and tetraphenylphosphonium bromide, the latter is particularly preferably usable.

The blending proportion of the above-mentioned quaternary ammonium salt or quaternary phosphonium salt is preferably 1 to 500 mmol, more preferably 3 to 200 mmol, particularly preferably 5 to 100 mmol per 1 mol of glycidol. The amount of the aforesaid quaternary ammonium salt represented by the general formula (V) or quaternary phosphonium salt represented by the general formula (VI) to be used is preferably 0.1 to 10 mol, more preferably 0.3 to 8 mol, particularly preferably 0.5 to 2 mol per 1 mol of the KX represented by the general formula (IV).

The concentration of the aqueous solution containing the aforesaid KX and the quaternary ammonium salt or quaternary phosphonium salt is preferably 5 to 80%, more preferably 20 to 60%, particularly preferably 30 to 50% by weight.

The catalyst deactivator represented by the general formula (III) is preferably at least one member selected from the group consisting of an alkali metal salt (excluding potassium salt) and alkaline earth metal salt of any of an alkylsulfonic acid, alkylbenzenesulfonic acid, phosphotungstic acid and phosphomolybdic acid, and specific examples of preferably usable ones include at least one member selected from sodium p-toluenesulfonate, sodium phosphotungstate and sodium phosphomolybdate. The amount of the catalyst deactivator to be used is preferably 1 to 1,000 mmol, more preferably 3 to 200 mmol, particularly preferably 5 to 100 mmol per 1 mol of glycidol.

In the third process of the present invention, the compound represented by the general formula (IV) and the quaternary ammonium salt represented by the general formula (V) or the quaternary phosphonium salt represented by the general formula (VI) are made to be present, as a catalyst, in the reaction system containing glycidol and methyl methacrylate, etc. to cause the transesterification. The catalyst deactivator represented by the general formula (III) to be added to the reaction system upon the completion of the reaction functions so as to deactivate the aforesaid transesterification catalyst.

The KX represented by the general formula (IV) to be used in the third process of the present invention is preferably potassium cyanide, potassium methacrylate, potassium acetate, potassium formate, potassium benzoate or potassium thiocyanate and is added to the reaction system in an amount of preferably 1 to 500 mmol, more preferably 3 to 100 mmol, particularly preferably 5 to 50 mmol per 1 mol of glycidol.

Of the above-exemplified preferable quaternary ammonium salts represented by the general formula (V) including tetramethylammonium chloride, trimethylethylammonium chloride, dimethyldiethylammonium chloride, methyltriethylammonium chloride, tetraethylammonium chloride, trimethylbenzylammonium chloride and triethylbenzylammonium chloride, there are particularly preferably usable tetramethylammonium chloride, methyltriethylammonium chloride, tetraethylammonium chloride and triethylbenzylammonium chloride.

Of the above-exemplified preferable quaternary phosphonium salt represented by the general formula (VI) including tetramethylphosphonium iodide and tetraphenylphosphonium bromide, the latter is particularly preferably usable.

The blending proportion of the above-mentioned quaternary ammonium salt or quaternary phosphonium salt is preferably 1 to 500 mmol, more preferably 3 to 100 mmol, particularly preferably 5 to 100 mmol per 1 mol of glycidol.

The catalyst deactivator represented by the general formula (III) is preferably at least one member selected from the group consisting of a sodium salt and calcium salt of any of an alkylsulfonic acid, alkylbenzenesulfonic acid, phosphotungstic acid and phosphomolybdic acid, and specific examples of preferably usable ones include at least one member selected from sodium p-toluenesulfonate, sodium phosphotungstate and sodium phosphomolybdate. The amount of the catalyst deactivator to be used is preferably 1 to 500 mmol, more preferably 3 to 100 mmol, particularly preferably 5 to 100 mmol per 1 mol of glycidol.

In the following, the present invention will be described in more detail with reference to comparative examples and examples, which however, shall not be construed to limit the present invention thereto. In the examples and comparative examples, all the purities (%) of starting raw materials and objective products that were determined by "GC" method are shown in % by weight.

Preparation Example of tetramethylammonium methacrylate.

In a 100 milliliter (hereinafter abbreviated to "mL") autoclave were placed 27.2 g of methyl methacrylate, 15.3 g of trimethylamine and 40 g of methanol under heating and shaking. After the temperature inside the autoclave reached 170° C., the reaction was continued at 170° C. for 3 hours. Upon completion of the reaction, the content in the autoclave was cooled, brought back to atmospheric pressure and analyzed. As a result, tetramethylammonium methacrylate was obtained in a yield of 76 mol % (based on trimethylamine).

EXAMPLE 1

In a 2 liter (hereinafter abbreviated to "L") five-necked flask equipped with a gas introduction pipe, a thermometer, a stirrer, a distillation column with 15 mm inside diameter and 300 mm length packed inside with McMahon packings and fitted at the top with a reflux ratio controller and a sampling pipe were placed 500 g (5 mol) of methyl methacrylate, 74 g (1 mol) of glycidol, 0.5 g of p-methoxyphenol and 0.714 g (8.5 mmol) of tetraethylammonium cyanide (produced by ALDRICH Corporation). Then heating was started under a reduced pressure of 300 mm Hg. Refluxing was started at a kettle (flask) temperature of 70° C., the reflux ratio was controlled to 10 to 30 so that the column top temperature was in the range of 38° to 55° C., and the methanol thus formed was distilled away as an azeotrope with methyl methacrylate. After 3 hours from the start of the reaction, the kettle temperature was raised to 74° C., when the reaction was arrested. The kettle temperature of 74° C. was confirmed by that the column top temperature could no longer be controlled to 55° C. or lower and at the same time, the conversion of glycidol was proved to be 99.5% by means of gas chromatography.

Immediately after the completion of the reaction, the reflux ratio controller and the McMahon packings were detached from the distillation column, 5.6 g (51 mmol) of sodium p-toluenesulfonate was added into the kettle to deactivate the catalyst and the kettle inside pressure was reduced to 100 mm Hg to distill and recover excess methyl methacrylate. Subsequently, the pressure was reduced to 30 to 4 mm Hg to recover 30.2 g of the initial boiling component, which contained 4.6% of glycidol but was usable as the next starting raw material of synthesis. The principal distillate was recoverd in an amount of 97 g and contained glycidyl methacrylate with 98.7% purity and 0.3% of glycidol.

EXAMPLE 2

The procedure in Example 1 was repeated except that there was used as a catalyst, 1.591 g (10 mmol) of tetramethylammonium methacrylate which had been produced in the above-mentioned Preparation Example in place of tetraethylammonium cyanide. The reaction was finished after 2 hours from the start thereof. Thus glycidyl methacrylate was obtained by means of distillation in a purity of 98.0% with 0.9% of glycidol at a conversion of glycidol of 98.4%.

EXAMPLE 3

The procedure of Example 1 was repeated except that there was used as a catalyst, 3.12 g (10 mmol) of tetrabutylammonium thiocyanate (produced by ALDRICH corporation) in place of tetraethylammonium cyanide. The reaction was finished after 3 hours from the start thereof. The conversion of glycidol was proved to be 98.7% as a result of analysis by gas chromatography.

Immediately after the completion of the reaction, 7.2 g (26 mmol) sodium phosphotungstate was added into the flask and distillation was carried out in the same manner as in Example 1. Thus, glycidyl methacrylate was obtained in a purity of 98.5% with 0.7% of glycidol.

COMPARATIVE EXAMPLE 1

The reaction was carried out in the same manner as in Example 1 except that 0.55 g (8.5 mmol) of potassium cyanide alone was used as a catalyst. As a result, 99% conversion of glycidol was attained but after the completion of the reaction, black oily impurity was found. Then, distillation was carried out in the same manner as in Example 1 except that the addition of sodium p-toluenesulfonate was omitted. As a result, glycidol was by produced during the course of distillation, and accordingly, glycidyl methacrylate as the objective product was obtained in a purity of 95.0% and in a remarkably low yield of only 65 g.

COMPARATIVE EXAMPLE 2

The reaction was carried out in the same manner as in Example 1 except that 0.55 g (8.5 mmol) of potassium cyanide was used as a catalyst. As a result, the by-production of glycidol during the course of distillation could not be suppressed at all. As a result, glycidyl methacrylate as the objective product was obtained in a purity of 94.0%.

COMPARATIVE EXAMPLE 3

The procedure in Comparative Example 1 was repeated to carry out the reaction except that 0.714 g of tetraethylammonium cyanide was used in place of potassium cyanide. As a result, 99% conversion of glycidol was attained, but the by-production of glycidol during the course of distillation could not be suppressed at all, and the resultant glycidyl methacrylate had a purity of 94%.

COMPARATIVE EXAMPLE 4

The procedure in Example 1 was repeated to carry out the reaction except that 1.86 g (17 mmol) of tetramethylammonium chloride was used. In spite of transesterification being tried for 2 hours, the reaction hardly proceeded, and thus, the distillation procedure was omitted.

Table 1 (1) and (2) give the reactional conditions and the results of Examples 1 to 3 and Comparative Examples 1 to 4.

TABLE 1 (1)

|  | Example 1 | Example 2 | Example 3 |
|---|---|---|---|
| Methyl metacrylate (MMA) (g) | 500 | 500 | 500 |
| Glycidol (g) | 74 | 74 | 74 |
| Potassium salt (g) | — | — | — |
| Quaternary amonium salt (g) | TEACy 0.714 | TMAM 1.591 | TBAT 3.12 |
| Catalyst deactivator (g) | PTSS 5.6 | PTSS 5.6 | PWS 7.2 |
| Conversion of glycidol (%) | 99.5 | 98.4 | 98.7 |
| Product purity (%) | 98.7 | 98.0 | 98.5 |
| Glycidol concentration (%) | 0.3 | 0.9 | 0.7 |

TABLE 1 (2)

|  | Comparative Example 1 | Comparative Example 2 | Comparative Example 3 | Cmparative Example 4 |
|---|---|---|---|---|
| Methyl metacrylate (MMA) (g) | 500 | 500 | 500 | 500 |
| Glycidol (g) | 74 | 74 | 74 | 74 |
| Potassium salt (g) | 0.55 | 0.55 | — | — |
| Quaternary ammonium salt (g) | — — | — — | THACY 0.714 | TMAC 1.86 |
| Catalyst deactivator (g) | — — | PTSS 5.6 | — — | — — |
| Conversion of glycidol (%) | 99.0 | 98.1 | 99.0 | — |
| Product purity (%) | 95.0 | 94.0 | 94.0 | — |
| Glycidol concentration (%) | 3.1 | 2.8 | 3.2 | — |

Remarks:
TEACy tetraethylammonium cyanide
TMAM tetramethylammonium methacrylate
TBAT tetrabutylammonium thiocyanate
PTSS sodium p-toluenesulfonate
PWS sodium phosphotungstate
TMAC tetramethylammonium chloride

EXAMPLE 4

In a 2 L five-necked flask equipped with a gas introduction pipe, a thermometer, a stirrer, a distillation column with 15 mm inside diameter and 300 mm length packed inside with McMahon packings and fitted at the top with a reflux ratio controller and a sampling pipe were placed 500 g (5 mol) of methyl methacrylate, 0.5 g of p-methoxyphenol and previously prepared 50% aqueous solution containing 0.55 g (8.5 mmol) of potassium cyanide and 0.93 g (8.5 mmol) of tetramethylammonium chloride (produced by Nihon Tokushu Kagaku Kogyo K.K.). Then heating was started under a reduced pressure of 300 mm Hg. Heating was continued until the column top temperature reached 80° C. and water was distilled away as the azeotrope with methyl methacrylate. When the kettle was cooled to 70° C., 74 g (1 mol) of glycidol was collectively added to the reaction system, followed by the resumption of heating. Refluxing was started at a kettle (flask) temperature of 70° C., the reflux ratio was controlled to 10 to 30 so that the column top temperature was in the range of 38° to 55° C. and the methanol thus formed was distilled away as an azeotrope with methyl methacrylate. After 2.5 hours from the start of the reaction, the kettle temperature was raised to 74° C., when the reaction was arrested. Whereupon, the conversion of glycidol was proved to be 99% by means of gas chromatography.

Immediately after the completion of the reaction, the reflux ratio controller and the McMahon packings were detached from the distillation column, 5.6 g (51 mmol) of sodium p-toluenesulfonate was added into the kettle to deactivate the catalyst and the kettle inside pressure was reduced to 100 mm Hg to distill and recover excess methyl methacrylate. Subsequently, the pressure was reduced to 30 to 4 mm Hg to recover 30 g of the initial boiling component, which contained 4.5% of glycidol but was usable as the next starting raw material of synthesis. The principal distillate was recovered in an amount of 99 g and contained glycidyl methacrylate with 99.0% purity and 0.7% of glycidol.

EXAMPLE 5

The procedure of Example 4 was repeated to carry out the reaction except that to the reaction system was added as a catalyst, 30% aqueous solution containing 1.24 g (10 mmol) of potassium methacrylate and 1.657 (10 mmol) of tetraethylammonium chloride (produced by Lion Akzo Co., Ltd.). The reaction was finished after 2 hours from the start thereof. Thus glycidyl methacrylate was obtained by means of distillation in a purity of 98.3% with 0.9% of glycidol at a conversion of glycidol of 98.5%.

EXAMPLE 6

In a 2 L five-necked flask equipped with a gas introduction pipe, a thermomether, a stirrer, a distillation column with 15 mm inside diameter and 300 mm length packed inside with McMahon packings and fitted at the top with a reflux ratio controller and a sampling pipe were placed 500 g (5 mol) of methyl methacrylate, 74 g (1 mol) of glycidol, 0.5 g of p-methoxyphenol and previously prepared 40% aqueous solution containing 0.981 g (10 mmol) of potassium acetate and 1.096 g (10 mmol) of tetramethylammonium chloride. Then heating was started under a reduced pressure of 300 mm Refluxing was started at a kettle (flask) temperature of 70° C., the reflux ratio was controlled to 10 to 30 so that the column top temperature was in the range of 38° to 55° C., and the methanol thus formed was distilled away as an azeotrope with methyl methacrylate. After 3 hours from the start of the reaction, the kettle temperature was raised to 74° C., when the reaction was arrested. Whereupon, the conversion of glycidol was proved to be 98.8% by means of gas chromatography.

Immediately after the completion of the reaction, the reflux ratio controller and the McMahon packings were detached from the distillation column, 11.2 g (102 mmol) of sodium p-toluenesulfonate was added into the kettle to deactivate the catalyst and the kettle inside pressure was reduced to 100 mm Hg to distill and recover excess methyl methacrylate. Subsequently, the pressure was reduced to 30 to 4 mm Hg to recover 28 g of the initial boiling component, which contained 4.8% of glycidol but was usable as the next starting raw material of synthesis. The principal distillate was recovered in an amount of 103 g and contained glycidyl methacrylate with 98.6% purity and 0.5% of glycidol.

EXAMPLE 7

The reaction was carried out in the same manner as in Example 4 except that to the reaction system was added 50% aqueous solution containing 0.83 g (8.5 mmol) of potassium thiocyanate and 1.578 g (8.5 mmol) of benzyltrimethylammonium chloride in place of 50% aqueous solution containing potassium cyanide and tetramethylammonium cholorde. Then, heating was started under a reduced pressure of 300 mm Hg and, when the kettle temperature reached 70° C., dropwise addition of glycidol was started to start the reaction. The reflux ratio was controlled to 10 top 30 so that the column top temperature was in the range of 38° to 55° C., and the methanol thus formed was distilled away as an azeotrope with methyl methacrylate. The dropwise addition of 74 g (1 mol) of glycidol was completed over a period of 30 minites. The reaction was finished after 3.5 hours from the start thereof at a conversion of glycidol of 98.3%. Immediately thereafter, the reflux ratio controller and the McMahon packings were detached from the column, 7.2 g (26 mmol) of sodium phosphotungstate was added into the kettle to deactivate the catalyst. Subsequently, distillation was carried out in the same manner as in Example 4. As a result, glycidyl methacrylate was obtained in a purity of 98.1% with 1.1% glycidol.

COMPARATIVE EXAMPLE 5

The procedure in Comparative Example 1 was repeated to carry out the reaction except that 1.1 g of 50% aqueous solution of potassium cyanide (8.5 mmol) was used. As a result, 99% conversion of glycidol was attained but after the completion of the reaction, black oily impurity was found and glycidol was by-produced during the course of distillation. Thus glycidyl methacrylate with 95.0% purity was obtained in a remarkably low yield of only 65 g.

COMPARATIVE EXAMPLE 6

The procedure in Comparative Example 2 was repeated to carry out the reaction except that 1.375 g of 40% aqueous solution of potassium cyanide (8.5 mmol) was used. As a result, 98.1% conversion of glycidol was attained but the by-production of glycidol during the course of distillation could not be suppressed at all, and the resultant glycidyl methacrylate had purity of 94%.

COMPARATIVE EXAMPLE 7

The procedure in Comparative Example 4 was repeated to carry out the reaction except that 6.29 of 30% aqueous solution of tetramethylammonium chloride (17 mmol) was used. In spite of the transesterification being tried for 2 hours, the reaction hardly proceeded, and thus the distillation procedure was omitted.

Table 2 (1) and (2) give the reactional conditions and the results of Examples 4 to 7 and Comparative Examples 5 to 7.

TABLE 2 (1)

|  | Example 4 | Example 5 | Example 6 | Example 7 |
| --- | --- | --- | --- | --- |
| Methyl metacrylate (MMA) (g) | 500 | 500 | 500 | 500 |
| Glycidol (g) | 74 | 74 | 74 | 74 |
| Potassium salt | KCN | KMA | KAC | KTC |
| (g) | 0.55 | 1.24 | 0.981 | 0.83 |
| Quaternary ammonium salt | TMAC | TEAC | TMAC | BTMAC |
| (g) | 0.93 | 1.657 | 1.096 | 1.578 |
| Concentration of catalyst aqueous solution (%) | 50 | 30 | 40 | 50 |
| Catalyst deactivator | PTSS | PTSS | PTSS | PWS |
| (g) | 5.6 | 5.6 | 11.2 | 7.2 |

TABLE 2 (1)-continued

|  | Example 4 | Example 5 | Example 6 | Example 7 |
| --- | --- | --- | --- | --- |
| Conversion of glycidol (%) | 99 | 98.5 | 98.8 | 98.3 |
| Product purity (%) | 99.0 | 98.3 | 98.6 | 98.1 |
| Glycidol concentration (%) | 0.7 | 0.9 | 0.5 | 1.1 |

TABLE 2 (2)

|  | Comparative Example 5 | Comparative Example 6 | Comparative Example 7 |
| --- | --- | --- | --- |
| Methyl metacrylate (MMA) (g) | 500 | 500 | 500 |
| Glycidol (g) | 74 | 74 | 74 |
| Potassium salt | KCN | KCN | — |
| (g) | 0.55 | 0.55 | — |
| Quaternary amonium salt | — | — | TMAC |
| (g) | — | — | 1.86 |
| Concentration of catalyst aqueous solution (%) | 50 | 40 | 30 |
| Catalyst deactivator | — | PTSS | — |
| (g) | — | 5.6 | — |
| Conversion of glycidol (%) | 99 | 98.1 | — |
| Product purity (%) | 95.0 | 94.0 | — |
| Glycidol concentration (%) | 3.1 | 2.8 | — |

Remarks:
KCN potassium cyanide
KMA potassium methacrylate
KAC potassium acetate
KTC potassium thiocyanate
TMAC tetramethylammonium chloride
TEAC tetraethyl ammonium chloride
BTMAC benzyltrimethylammonium chloride
PTSS sodium p-toluenesulfonate
PWS sodium phosphotungstate

EXAMPLE 8

In a 2 L five-necked flask equipped with a gas introduction pipe, a thermometer, a stirrer, a distillation column with 15 mm inside diameter and 300 mm length packed inside with McMahon packings and fitted at the top with a reflux ratio controller and a sampling pipe were placed 500 g (5 mol) of methyl methacrylate, 74 g (1 mol) of glycidol, 0.55 g (8.5 mmol) of potassium cyanide and 1.86 g (17 mmol) of tetramethylammonium chloride and 0.5 g of p-methoxyphenol. Then heating was started under a reduced pressure of 300 mm Hg. Refluxing was started at a kettle (flask) temperature of 70° C., the reflux ratio was controlled to 10 to 30 so that the column top temperature was in the range of 38° to 55° C., and the methanol thus formed was distilled away as an azeotrope with methyl methacrylate. After 3.5 hours from the start of the reaction, the kettle temperature was raised to 74° C., when the reaction was arrested. The kettle temperature of 74° C. was confirmed by that the column top temperature could no longer be controlled to 55° C. or lower and at the same time, the conversion of glycidol was proved to be 99% by means of gas chromatography.

Immediately after the completion of the reaction, the reflux ratio controller and the McMahon packings were detached from the distillation column, 5.6 g (51 mmol) of sodium p-toluenesulfonate was added into the kettle to deactivate the catalyst and the kettle inside pressure was reduced to 100 mm Hg to distill and recover excess methyl methacrylate. Subsequently, the pressure was reduced to 30 to 4 mm Hg to recover 31 g of the initial boiling component, which contained 4.8% of glycidol but was usable as the next starting raw material of synthesis. The principal distillate was recovered in an amount of 98 g and contained glycidyl methacrylate with 98.3% purity and 0.8% of glycidol.

EXAMPLE 9

The procedure in Example 8 was repeated except that the feed amounts of both the catalyst and the catalyst deactivator were halved. The reaction was finished after 5 hours from the start thereof. Thus glycidyl methacrylate was obtained by means of distillation in a purity of 98.0% with 0.9% of glycidol at conversion of glycidol of 98%.

EXAMPLE 10

The procedure in Example 8 was repeated except that the feed amounts of both the catalyst and the catalyst deactivator were doubled. The reaction was finished after 3 hours from the start thereof. Thus glycidyl methacrylate was obtained by means of distillation in a purity of 98.5% with 0.7% of glycidol at a conversion of glycidol of 99%.

EXAMPLE 11

The procedure of Example 8 was repeated except that there was used as a catalyst, 0.83 g (8.5 mmol) of potassium thiocyanate in place of potassium cyanide. The reaction was finished after 3.5 hours from the start thereof. Whereupon the coversion of glycidol was proved to be 99%.

Immediately after the completion of reaction, 5.6 g (51 mmol) of sodium p-toluenesulfonate was added into the flask and distillation was carried out in the same manner as in Example 8. Thus, glycidyl methacrylate was obtained in a purity of 98.2% with 0.9% of glycidol.

COMPARATIVE EXAMPLE 8

In a 2 L five-necked flask equipped with a gas introduction pipe, a thermometer, a stirrer, a distillation column with 15 mm inside diameter and 300 mm length packed inside with McMahon packings and fitted at the top with a reflux ratio controller and a sampling pipe were placed 500 g (5 mol) of methyl methacrylate, 74 g (1 mol) of glycidol, 0.55 g (8.5 mmol) of potassium cyanide, 1.86 g (17 mmol) of tetramethylammonium chloride and 0.5 g of p-methoxyphenol. Then heating was started under a reduced pressure of 300 mm Hg. Refluxing was started at a kettle (flask) temperature of 70° C., the reflux ratio was controlled to 10 to 30 so that the column top temperature was in the range of 38° to 55° C., and the methanol thus formed was distilled away as an azeotrope with methyl methacrylate. After 3.2 hours from the start of the reaction, the kettle temperature was raised to 74° C., when the reaction was arrested. The kettle temperature of 74° C. was confirmed by that the column top temperature could no longer be controlled to 55° C. or lower and at the same time, the conversion of glycidol was proved to be 99% by means of gas chromatography.

Immediately after the completion of the reaction, the reflux ratio controller and the McMahon packings were detached from the distillation column, and the kettle inside pressure was reduced to 100 mm Hg to distill and recover excess methyl methacrylate. Subsequently, the pressure was reduced to 30 to 4 mm Hg to recover 28 g of the initial boiling component, which contained 5.0% of glycidol but was usable as the next starting raw material of synthesis. The principal distillate was recovered in an amount of 102 g and contained glycidyl methacrylate with 92.0% purity and 4.8% of glycidol.

Table 3 (1) and (2) give the reactional conditions and the results of Examples 8 to 11 and Comparative Examples 8 and 9.

TABLE 3 (1)

|  | Example 8 | Example 9 | Example 10 | Example 11 |
|---|---|---|---|---|
| Methyl metacrylate (MMA) (g) | 500 | 500 | 500 | 500 |
| Glycidol (g) | 74 | 74 | 74 | 74 |
| Potassium salt | KCN | KCN | KCN | KTC |
| (g) | 0.55 | 0.275 | 1.1 | 0.83 |
| Quaternary amonium salt | TMAC | TMAC | TMAC | TMAC |
| (g) | 1.86 | 0.93 | 3.72 | 1.86 |
| Catalyst deactivator | PTST | PTSS | PTSS | PTSS |
| (g) | 5.6 | 2.8 | 11.2 | 5.6 |
| Conversion of glycidol (%) | 99 | 98 | 99 | 99 |
| Product purity (%) | 98.3 | 98.0 | 98.5 | 98.2 |
| Glycidol concentration (%) | 0.8 | 0.9 | 0.7 | 0.9 |

TABLE 3(2)

|  | Comparative Example 8 |
|---|---|
| Methyl metacrylate (MMA) (g) | 500 |
| Glycidol (g) | 74 |
| Potassium salt | KCN |
| (g) | 0.55 |
| Quaternary amonium salt | TMAC |
| (g) | 1.86 |
| Catalyst deactivator | — |
| (g) | — |
| Conversion of glycidol (%) | 99 |
| Product purity (%) | 92.0 |
| Glycidol concentration (%) | 4.8 |

Remarks:
KCN potassium cyanide
KTC potassium thiocyanate
TMAC tetramethylammonium chloride
PTSS sodium p-toluenesulfonate

What is claimed is:

1. A process for producing glycidyl acrylate or glycidyl methacrylate by the transesterification of glycidol and methyl acrylate or methyl methacrylate which process comprises carrying out the transesterification in the presence of a polymerization inhibitor by the use of a catalyst selected from the group consisting of a quaternary ammonium salt represented by the general formula (I) and a quaternary phosphonium salt represented by the general formula (II)

$$(R^1R^2R^3R^4)NX \qquad (I)$$

$$(R^1R^2R^3R^4)PX \qquad (II)$$

wherein $R^1$, $R^2$, $R^3$ and $R^4$ are each an alkyl group having 1 to 20 carbon atoms, an alkenyl group or a phenyl group and X is a cyanide ion, a cyanate ion, an organocarboxylate ion or a thiocyanate ion, to complete the reaction; thereafter arresting the reaction by adding to the reaction system, a catalyst deactivator represented by the general formula (III)

$$SB \qquad (III)$$

wherein S is a sulfonic acid or a heteropolyacid and B is an alkali metal with the proviso that potassium is excluded therefrom or an alkaline earth metal; and distilling away unreacted methyl acrylate or methyl methacrylate under reduced pressure to separate glycidyl acrylate or glycidyl methacrylate.

2. The process according to claim 1 wherein the quaternary ammonium salt represented by the general formula (I) is at least one member selected from the group consisting of tetramethylammonium cyanide, tetramethylammonium acetate, tetraethylammonium acetate, tetraethylammonium cyanide, tetrabutylammonium acetate, tetrabutylammonium cyanide, tetrabutylammonium thiocyanate, trimethylethylammonium cyanide, dimethyldiethylammonium acetate, methyltriethylammonium thiocyanate, trimethylbenzylammonium acetate, triethylbenzylammonium cyanide and tetramethylammonium methacrylate and the quaternary phosphonium salt represented by the general formula (II) is at least one member selected from the group consisting of tetramethylphosphonium methacrylate and tetraphenylphosphonium cyanide.

3. The process according to claim 1 wherein X in the general formula (I) and (II) is an organocarboxylate ion and said organocarboxylate ion is at least one member selected from the group consisting of formate ion, acetate ion, propionate ion, methacrylate ion and benzoate ion.

4. The process according to claim 1 wherein the amount of the quaternary ammonium salt represented by the general formula (I) or the quaternary phosphonium salt represented by the general formula (II) to be used in the catalyst is 1 to 500 mmol per 1 mol of the glycidol.

5. The process according to claim 1 wherein the catalyst deactivator represented by the general formula (III) is at least one member selected from the group consisting of an alkali metal salt excluding potassium salt of an alkylsulfonic acid, an alkylbenzenesulfonic acid, a phosphotungstic acid and a phosphomolybdic acid and an alkaline earth metal salt of an alkylsulfonic acid, an alkylbenzenesulfonic acid, a phosphotungstic acid and a phosphomolybdic acid, and the amount of the metal salt to be used is 1 to 1000 mmol per 1 mol of the glycidol.

6. A process for producing glycidyl acrylate or glycidyl methacrylate by the transesterification of glycidol and methyl acrylate or methyl methacrylate which process comprises carrying out the transesterfication in the presence of a polymerization inhibitor by the use of as a catalyst, an aqueous solution containig KX represented by the general formula (IV)

$$KX \quad (IV)$$

wherein K is potassium and X is a cyanide ion, a cyanate ion, an organocarboxylate ion or a thiocyanate ion, and a salt selected from the group consisting of quaternary ammonium salt represented by the general formula (V) and a quaternary phosphonium salt represented by the general formula (VI)

$$(R^1R^2R^3R^4)NY \quad (V)$$

$$(R^1R^2R^3R^4)PY \quad (VI)$$

wherein $R^1$, $R^2$, $R^3$ and $R^4$ are each an alkyl group having 1 to 20 carbon atoms, an alkenyl group or a phenyl group and Y is iodine, bromine or chlorine, to complete the reaction; thereafter arresting the reaction by adding to the reaction system, a catalyst deactivator represented by the general formula (III)

$$SB \quad (III)$$

wherein S is a sulfonic acid or a heteropolyacid and B is an alkali metal with the proviso that potassium is excluded therefrom or an alkaline earth metal; and distilling away unreacted methyl acrylate or methyl methacrylate under reduceu pressure to separate glycidyl acrylate or glycidyl methacrylate.

7. The process according to claim 6 wherein the KX represented by the general formula (IV) is at least one member selected from the group consisting of potassium cyanide, potassium cyanate, potassium thiocyanate, potassium formate, potassium acetate, potassium propionate, potassium methacrylate and potassium benzoate, and the amount of the KX to be used in the catalyst is 1 to 500 mmol per 1 mol of the glycidol.

8. The process according to claim 6 wherein the quaternary ammonium salt represented by the general formula (V) is at least one member selected from the group consisting of tetramethylammonium chloride, trimethylethylammonium chloride, dimethyldiethylammonium chloride, methyltriethylammonium chloride, tetraethylammonium chloride, trimethylbenzylammonium chloride and triethylbenzylammonium chloride and the quaternary phosphonium salt is at least one member selected from the group consisting of tetramethylphosphonium iodide and tetraphenylphosphonium bromide.

9. The process according to claim 6 wherein the amount of the quaternary ammonium salt represented by the general formula (V) or the quaternary phosphonium salt represented by the general formula (VI) to be used in the catalyst is 1 to 500 mmol per 1 mol of the glycidol.

10. The process according to claim 6 wherein the catalyst deactivator represented by the general formula (III) is at least one member selected from the group consisting of an alkali metal salt excluding potassium salt of an alkylsulfonic acid, an alkylbenzenesulfonic acid, a phosphotungstic acid and a phosphomolybdic acid and an alkaline earth metal salt of an alkylsulfonic acid, an alkylbenzenesulfonic acid, a phosphotungstic acid and a phosphomolybdic acid, and the amount of the metal salt to be used is 1 to 1000 mmol per 1 mol of the glycidol.

11. The process according to claim 6 wherein the amount of the quaternary ammonium salt represented by the general formula (V) or the quaternary phosphonium salt represented by the general formula (VI) to be used in the catalyst is 0.1 to 10 moles per 1 mol of the KX represented by the general formula (IV) and the mixed aqueous solution has a concentration in the range of 5 to 80% by weight.

12. A process for producing glycidyl acrylate or glycidyl methacrylate by the transesterification of glycidol and methyl acrylate or methyl methacrylate which process comprises carrying out the transesterification in the presence of a polymerization inhibitor by the use of a catalyst comprising KX represented by the general formula (IV)

$$KX \quad (IV)$$

wherein K is potassium and X is a cyanide ion, a cyanate ion, an organocarboxylate ion or a thiocyanate ion, and a salt selected from the group consisting of a quaternary ammonium salt represented by the general formula (V) and a quaternary phosphonium salt represnted by the general formula (VI)

$$(R^1R^2R^3R^4)NY \quad (V)$$

$$(R^1R^2R^3R^4)PY \quad (VI)$$

wherein $R^1$, $R^2$, $R^3$ and $R^4$ are each an alkyl group having 1 to 20 carbon atoms, an alkenyl group or a phenyl group and Y is iodine, bromine or chlorine, to complete the reaction; thereafter arresting the reaction by adding to the reaction system, a catalyst deactivator represented by the general formula (III)

$$sB \quad (III)$$

wherein S is a sulfonic acid or a heteropolyacid and B is an alkali metal with the proviso that potassium is excluded therefrom or an alkaline earth metal; and distilling away unreacted methyl acrylate or methyl methacrylate under reduced pressure to separate glycidyl acrylate or glycidyl methacrylate.

13. The process according to claim 12 wherein X in the general formula (IV) is an organocarboxylate ion and said organocarboxylate ion is at least one member selected from the group consisting of formate ion, acetate ion, propionate ion, methacrylate ion and benzoate ion.

14. The process according to claim 12 wherein the KX represented by the general formula (IV) is at least one member selected from the group consisting of potassium cyanide and potassium thiocyanate, and the amount of the KX to be used in the catalyst is 1 to 500 mmol per 1 mol of the glycidol.

15. The process according to claim 12 wherein the quaternary ammonium salt represented by the general formula (V) is at least one member selected from the group consisting of tetramethylammonium chlorde, trimethylethylammonium chloride, dimethyldiethylammonium chloride, methyltriethylammonium chloride, tetraethylammonium chloride, trimethylbenzylammonium chloride and triethylbenzylammonium chloride and the quaternary phosphonium salt represented by the general formula (VI) is at least one member selected from the group consisting of tetramethylphosphonium iodide and tetraphenylphosphonium bromide, and the amount of the quaternary ammonium salt or the quaternary phosphonium salt to be used in the catalyst is 1 to 500 mmol per 1 mol of the glycidol.

16. The process according to claim 12 wherein the catalyst deactivator represented by the General formula (III) is at least one member selected from the Group consisting of a sodium salt of an alkylsulfonic acid, an alkylbenzenesulfonic acid, a phosphotungstic acid and phosphomolybdic acid and a calcium salt of an alkylsulfonic acid, an alkylbenzensulfonic acid, a phosphotungstic acid and phosphomolybdic acid, and the amount of the metal salt to be used is 1 to 500 mmol per 1 mol of the glycidol.

* * * * *